March 23, 1976 S. IWAMURA Plant Pat. 3,850
PLUM PLANT
Filed April 14, 1975
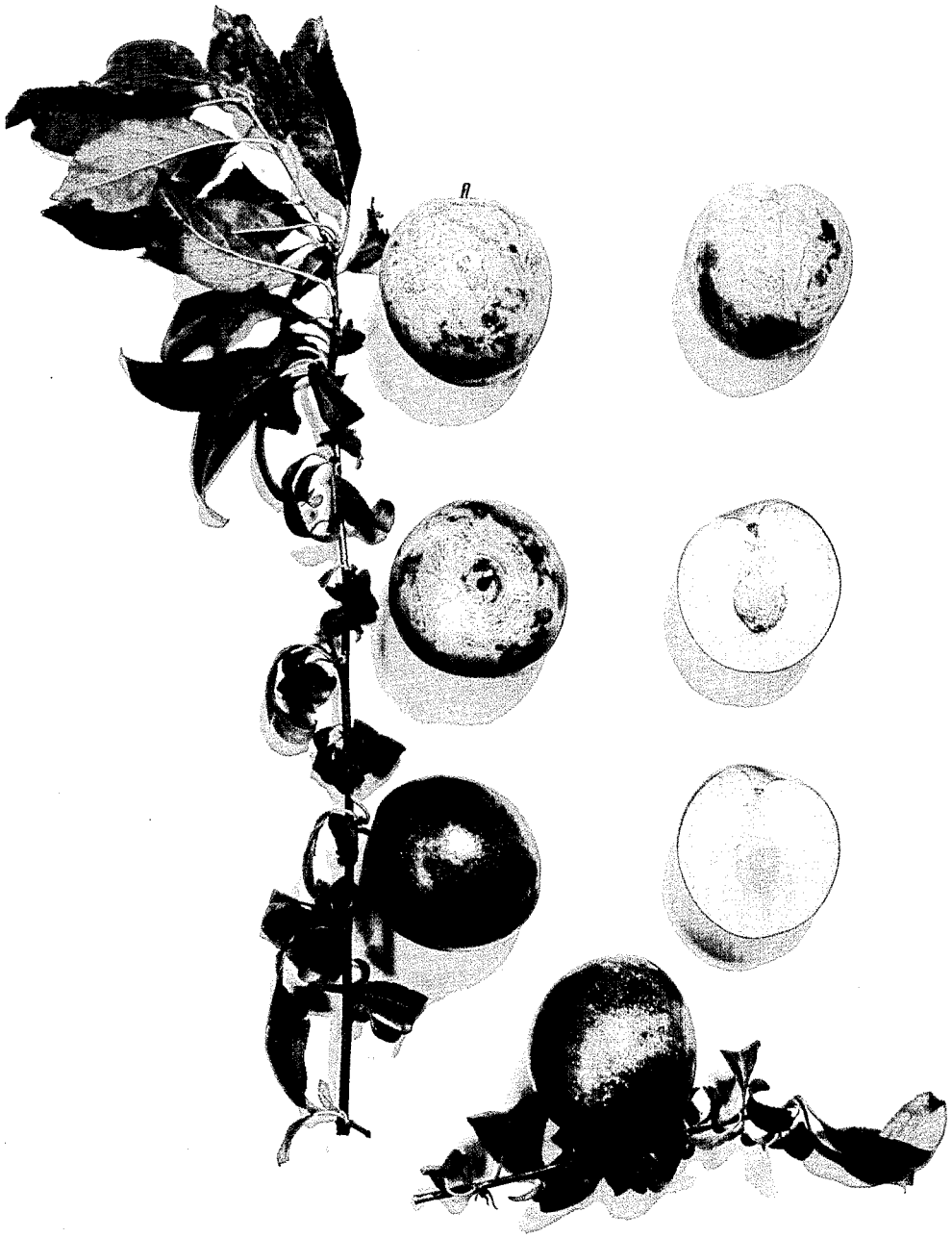

United States Patent

Plant Pat. 3,850

Patented Mar. 23, 1976

3,850

PLUM PLANT

Seishi Iwamura, 12430 E. South Ave., Parlier, Calif. 93648

Filed Apr. 14, 1975, Ser. No. 568,050

Int. Cl. A01h 5/03

U.S. Cl. Plt.—38 1 Claim

The present invention relates to a plum tree and more particularly to a new and distinct variety thereof broadly characterized by a tree of vigorous growth regularly bearing high quality fruit of firm texture and slightly acid flavor.

The instant variety has a commercially advantageous ripening period which occurs between the two major Santa Rosa varieties, Casselman (unpatented) and Roysum Plum (U.S. Pat. No. 2,619).

In 1971 I discovered the present variety of plum as a sport limb growing from a Roysum plum tree in my orchard near Parlier, Calif., having noted the principal characteristic of the fruit ripening three weeks earlier on the sport limb than the parent tree variety. The instant variety was asexually reproduced by budding it into trees of the Nemaguard variety whereby the resulting tree and fruit characteristics from such budding proved identical to the original sport.

The accompanying color photograph is of characteristic mature fruit of the subject variety bearing foliage and the mature fruits, and additionally showing a fruit of the subject variety divided on its suture plane to reveal uniform flesh coloration and stone.

Referring now more specifically to the pomological characteristics of this new and distinct variety of plum tree, the following is an outline description thereof observed under the ecological conditions prevailing in Fresno County, Calif. All major color plate identifications are by reference to Maerz and Paul, Dictionary of Color, Second Edition.

TREE

General: Vigorous, productive, self-pollinating, regular bearing.

Size: Large, may be pruned to vase shape.

Trunk: Medium size, medium scaliness with average furrows and ridges, orange color lenticels more numerous and more evenly distributed on the bark than the parent variety, consequently having an overall appearance of a lighter shade of brownish-grey.

LEAVES

Shape: Oblong-lanceolate to oblanceolate.

Size: Variable, medium thickness, averaging 2 to 4½ inches long and 1 to 2 inches wide.

Base: Tapered.

Apex: Acuminate.

Margin: Glandular, crenate.

Petiole: Medium length and thickness.

Glands: Averaging two at base of leaf.

Deciduous: Normal to the Santa Rosa variety.

Color: Smooth upper surface, dark green (22–L–8), surface vein light green (19–C–2); lower surface light green (22–L–8), somewhat lighter color than the parent tree leaves.

FLOWERS

Medium size when first blooming Feb. 24, 1974, average size and pollen when full bloom Mar. 3, 1974. White in color.

FRUIT

Season: Described at maturity. Ripe first week of September, last picking can be extended for a period of two weeks because of high quality of fruit.

Size: Variable, medium. 1⅞ to 2½ inches axially, average 2¼; 1¾ to 2½ inches at right angle to suture plane, average 2¼; 1¾ to 2½ inches transverse in suture plane, average 2 inches.

Form: Generally globose.

Suture: A shallow line extending from base to beyond and discontinuous at apex, with slight depression beyond the pistil point. No tendency to crack.

Base: Slightly truncated.

Stem: ⅜ to ½ inch long, 1/16 inch in diameter.

Skin: Medium thick, medium tender, tenacious to the flesh. Color, deep crimson shading with overladen bloom of blue (6–I–3 to 7–J–5), supplemented by light yellow specks (9–F–4) over the entire fruit characterizing the Santa Rosa variety, and with variable light yellow (9–F–4) lines, broken or joined at the vicinity of the base of the fruit and curving around stem area when fully colored.

Flesh: Light yellow (11–K–8) progressing to light orange-yellow when fruit becomes more mature. Texture is uniformly firm, ripens evenly; flavor is delicate, sweet, slightly more acid than the parent fruit.

STONE

Tenacity: Variable and spotty to the flesh.

Color: Light brown (13–L–10) with dark areas around the base, few with slight reddening of the base, apex, and along the ventral edge.

Size: ⅞ to 1½ inches in length, average 1 inch; 9/16 to ¾ inch in breadth, average ⅝ inch; ⅜ average thickness.

Generally: Pit is essentially identical to the parent as having the following characteristics: Obovate form, oval helum, acuminate apex, sides usually equal, fairly smooth surface and slightly furrowed near base, one small groove or none on dorsal edge, thick ventral edge with usually one groove.

USE

Markets: Nearby, and long distance.

Quality: Excellent eating quality with average acid flavor.

In substantially all of its characteristics except its ripening time of the fruit, the subject variety is virtually identical to that of the parent plum tree. This applies generally to its shape, size, and vigor, except that its lenticels are more numerous and more evenly distributed on the bark, consequently the overall appearance seems a shade lighter of brownish-grey and its fruit color, slightly darker purple, and the skin of the fruit has variable, light yellow lines broken or joined at the vicinity of the base and curving around the stem area when mature.

Although the new variety of plum possesses the described characteristics under the growing conditions near Parlier, Fresno County, Calif., in the San Joaquin Valley, it is to be understood that variations of the usual magnitude in the characteristics incident to the growing conditions, fertilization, pruning, thinning and pest control are to be expected.

Having thus described and photographed the distinct qualities of my new variety of plum tree, what is claimed is:

1. A new and distinct variety of plum tree substantially illustrated and described and particularly characterized as being a large size tree regularly bearing fruit of exceptionally firm, uniform quality, thereby particularly suited for long distance shipping, and distinguished from the parent plant, which it most nearly resembles, Roysum (U.S. Pat. No. 2,619) by ripening three weeks earlier, the harvest date being September 5, with the last picking extendable for two weeks because of the high quality fruit.

No references cited.

ROBERT E. BAGWELL, Primary Examiner